(12) United States Patent
Will

(10) Patent No.: US 9,068,225 B2
(45) Date of Patent: *Jun. 30, 2015

(54) FORMAT OF PROBES TO DETECT NUCLEIC ACID DIFFERENCES

(71) Applicant: Roche Molecular Systems, Inc., Pleasanton, CA (US)

(72) Inventor: Stephen G. Will, Cham (CH)

(73) Assignee: ROCHE MOLECULLAR SYSTEMS, INC., Pleasanton, CA (US)

( * ) Notice: Subject to any disclaimer, the term of this patent is extended or adjusted under 35 U.S.C. 154(b) by 78 days.

This patent is subject to a terminal disclaimer.

(21) Appl. No.: 13/786,749

(22) Filed: Mar. 6, 2013

(65) Prior Publication Data

US 2013/0266938 A1     Oct. 10, 2013

Related U.S. Application Data

(63) Continuation of application No. 12/852,936, filed on Aug. 9, 2010, now Pat. No. 8,409,802.

(60) Provisional application No. 61/234,189, filed on Aug. 14, 2009.

(51) Int. Cl.
| | | |
|---|---|---|
| *C12Q 1/68* | (2006.01) | |
| *C12P 19/34* | (2006.01) | |
| *C07H 21/02* | (2006.01) | |
| *C07H 21/04* | (2006.01) | |

(52) U.S. Cl.
CPC ............ *C12Q 1/6876* (2013.01); *C12Q 1/6827* (2013.01)

(58) Field of Classification Search
USPC ......... 435/6.1, 6.11, 6.12, 91.1, 91.2; 436/94, 436/501; 536/23.1, 24.3, 24.33
See application file for complete search history.

(56) References Cited

U.S. PATENT DOCUMENTS

| | | |
|---|---|---|
| 5,925,517 A | 7/1999 | Tyagi et al. |
| 6,103,476 A | 8/2000 | Tyagi et al. |
| 6,207,379 B1 | 3/2001 | Lee et al. |
| 6,383,752 B1 | 5/2002 | Agrawal et al. |
| 6,391,593 B1 | 5/2002 | Weston et al. |
| 2001/0019825 A1 | 9/2001 | Lee et al. |
| 2005/0123988 A1 | 6/2005 | Becker et al. |
| 2006/0110765 A1 | 5/2006 | Wang |
| 2007/0154914 A1 | 7/2007 | Gelfand et al. |
| 2008/0076131 A1 | 3/2008 | Chagovetz et al. |

FOREIGN PATENT DOCUMENTS

| | | |
|---|---|---|
| DE | 10356837 A1 | 6/2005 |
| EP | 10745171.8 | 5/2014 |
| WO | 9842873 A1 | 10/1998 |

OTHER PUBLICATIONS

Zhou, Luming, et al., 2004, "Closed-Tube Genotyping with Unlabled Oligonucleotide Probes and a Saturating DNA Dye", Clinical Chemistry, 50(8):1328-1335.

*Primary Examiner* — Frank Lu
(74) *Attorney, Agent, or Firm* — Olga Kay

(57) ABSTRACT

The invention provides, inter alia, novel probes, methods, reaction mixtures, and kits for detecting the presence or absence of a target nucleic acid sequence.

7 Claims, 5 Drawing Sheets

FORMAT OF PROBES TO DETECT NUCLEIC ACID DIFFERENCES

CROSS-REFERENCE TO RELATED APPLICATIONS

The present application is a continuation of the application Ser. No. 12/852,936, filed on Aug. 9, 2010, now U.S. Pat. No. 8,409,802 B2, which claims priority to a provisional application Ser. No. 61/234,189, filed on Aug. 14, 2009.

BACKGROUND OF THE INVENTION

A single nucleotide polymorphism (SNP) is a single base-pair mutation at a specific site in a genomic DNA sequence. SNPs are responsible for the majority of the DNA variations between two individuals. SNPs can predispose individuals to develop a certain disease or respond to a drug differently. Therefore, detection of SNPs can be used to monitor genetic conditions.

Gene variations and mutations also occur in pathogens, such as virus and bacteria. Detection of gene variations and mutations can be used to distinguish pathogens and in some cases can be helpful in predicting prognosis and course of treatment. Single base mutations also occur in somatic cells, for example during development and progression of cancer. Detecting these mutations is helpful in predicting response to therapy.

BRIEF SUMMARY OF THE INVENTION

The present invention provides for methods of detecting the presence or absence of a target nucleic acid sequence in a biological sample. In some embodiments, the method comprises:
a. contacting a detectably-labeled probe comprising an anchor nucleic acid domain and a reporter nucleic acid domain with the sample; and
b. detecting the presence or absence of binding of the probe to the target nucleic acid,
wherein the anchor and reporter domains are linked by a non-nucleoside linker, and neither the anchor nor the reporter domain forms a stem loop in the absence of the target nucleic acid;
and wherein
(i) the probe is not extendible by a polymerase;
(ii) the linker is linked to the anchor domain within 2 nucleotides of the 3' end of the anchor domain and the linker is linked to the reporter domain within 2 nucleotides of the 5' end of the reporter domain, wherein the anchor domain is not linked to a detectable label; and/or
(iii) the anchor domain and the reporter domain each comprise a contiguous sequence of at least 6 nucleotides complementary to the same strand of the target nucleic acid.

In some embodiments, the probe is not extendible by a polymerase

In some embodiments, the linker is linked to the anchor domain within 2 nucleotides of the 3' end of the anchor domain and the linker is linked to the reporter domain within 2 nucleotides of the 5' end of the reporter domain, wherein the anchor domain is not linked to a detectable label In some embodiments, the anchor domain and the reporter domain each comprise a contiguous sequence of at least 10 nucleotides complementary to one strand of the target nucleic acid In some embodiments, the detecting step comprises measuring the melting temperature of a complex formed between the reporter domain and the target nucleic acid.

In some embodiments, the length of the reporter domain is between 4 to 20 nucleotides. In some embodiments, the length of the reporter domain is between 6 to 12 nucleotides.

In some embodiments, the anchor region is between 6-40 nucleotides.

In some embodiments, the label is a fluorescent label. In some embodiments, the method further comprises contacting the probe and sample with a soluble intercalating quencher such that the quencher alters fluorescence from the label when the reporter domain forms a complex with the target nucleic acid.

In some embodiments, the target nucleic acid is a viral or microbial nucleic acid.

In some embodiments, the target nucleic acid is a human nucleic acid. In some embodiments, the human nucleic acid comprises a single nucleotide polymorphism (SNP) or a mutation and the reporter domain is 100% complementary to one allele of the SNP or the mutation.

In some embodiments, the probe comprises at least one non-natural nucleotide, wherein the non-natural nucleotide increases the melting temperature of the reporter domain compared to a corresponding natural nucleotide in the place of the non-natural nucleotide.

In some embodiments, the linker is polyethylene glycol. In some embodiments, the linker is hexa-ethylene glycol.

The present invention also provides for reaction mixtures for detecting the presence or absence of a target sequence. In some embodiments, the reaction mixture comprises:
a. a target nucleic acid comprising an anchor binding region and a reporter binding region, and
b. a detectably-labeled probe comprising an anchor nucleic acid domain and a reporter nucleic acid domain,
wherein the anchor and reporter domains are linked by a non-nucleoside linker, and neither the anchor nor the reporter domain forms a stem loop in the absence of the target nucleic acid, and
wherein
(i) the probe is not extendible by a polymerase;
(ii) the linker is linked to the anchor domain within 2 nucleotides of the 3' end of the anchor domain and the linker is linked to the reporter domain within 2 nucleotides of the 5' end of the reporter domain, wherein the anchor domain is not linked to a detectable label; and/or
(iii) the anchor domain and the reporter domain each comprise a contiguous sequence of at least 6 nucleotides complementary to the same strand of the target nucleic acid.

In some embodiments, the reaction mixture further comprises nucleoside triphosphates, a DNA polymerase, and/or an oligonucleotide primer.

In some embodiments, the probe is not extendible by a polymerase.

In some embodiments, the length of the reporter domain is between 4 to 20 nucleotides. In some embodiments, the length of the reporter domain is between 6 to 12 nucleotides.

In some embodiments, the anchor domain is between 6-40 nucleotides.

In some embodiments, the label is a fluorescent label. In some embodiments, a soluble intercalating quencher, wherein the quencher alters fluorescence from the label when the reporter domain forms a complex with the target nucleic acid.

In some embodiments, the target nucleic acid is a viral or microbial nucleic acid. In some embodiments, the target nucleic acid is a human nucleic acid. In some embodiments, the human nucleic acid comprises a single nucleotide polymorphism (SNP) or a mutation and the reporter domain is 100% complementary to one allele of the SNP or the mutation.

In some embodiments, the probe comprises at least one non-natural nucleotide, wherein the non-natural nucleotide increases the melting temperature of the reporter domain compared to a corresponding natural nucleotide in the place of the non-natural nucleotide.

In some embodiments, the linker is polyethylene glycol. In some embodiments, the linker is hexa-ethylene glycol.

The present invention also provides for a detectably-labeled probe comprising an anchor nucleic acid domain and a reporter nucleic acid domain, wherein:
the anchor and reporter domains are linked by a non-nucleoside linker;
neither the anchor nor the reporter domain forms a stem loop in the absence of the target nucleic acid; and
wherein:
(i) the probe is not extendible by a polymerase; and/or
(ii) the linker is linked to the anchor domain within 2 nucleotides of the 3' end of the anchor domain and the linker is linked to the reporter domain within 2 nucleotides of the 5' end of the reporter domain, wherein the anchor domain is not linked to a detectable label.

In some embodiments, the probe is not extendible by a polymerase.

In some embodiments, the linker is linked to the anchor domain within 2 nucleotides of the 3' end of the anchor domain and the linker is linked to the reporter domain within 2 nucleotides of the 5' end of the reporter domain, wherein the anchor domain is not linked to a detectable label.

In some embodiments, the length of the reporter domain is between 4 to 20 nucleotides. In some embodiments, the length of the reporter domain is between 6 to 12 nucleotides.

In some embodiments, the anchor domain is between 6-40 nucleotides.

In some embodiments, the label is a fluorescent label.

In some embodiments, the probe comprises at least one non-natural nucleotide, wherein the non-natural nucleotide increases the melting temperature of the reporter domain compared to a corresponding natural nucleotide in the place of the non-natural nucleotide.

In some embodiments, the linker is polyethylene glycol. In some embodiments, the linker is hexa-ethylene glycol.

The present invention also provides a kit for detecting the presence or absence of a target sequence. In some embodiments, the kit comprises:
a. a detectably-labeled probe comprising an anchor nucleic acid domain and a reporter nucleic acid domain, wherein:
 the anchor and reporter domains are linked by a non-nucleoside linker;
 neither the anchor nor the reporter domain forms a stem loop in the absence of the target nucleic acid; and
 wherein:
 (i) the probe is not extendible by a polymerase; and/or
 (ii) the linker is linked to the anchor domain within 2 nucleotides of the 3' end of the anchor domain and the linker is linked to the reporter domain within 2 nucleotides of the 5' end of the reporter domain, wherein the anchor domain is not linked to a detectable label; and
b. one or more reagents selected from the group consisting of a salt, a buffer, a nuclease inhibitor, nucleoside triphosphates, a DNA polymerase, and/or an oligonucleotide primer.

In some embodiments, the kit further comprises a soluble intercalating quencher such that the quencher alters fluorescence from the label when the reporter domain forms a complex with the target nucleic acid.

In some embodiments, the probe is not extendible by a polymerase.

In some embodiments, the length of the reporter domain is between 4 to 20 nucleotides. In some embodiments, the length of the reporter domain is between 6 to 12 nucleotides.

In some embodiments, the anchor domain is between 6-40 nucleotides.

In some embodiments, the label is a fluorescent label.

In some embodiments, the probe comprises at least one non-natural nucleotide, wherein the non-natural nucleotide increases the melting temperature of the reporter domain compared to a corresponding natural nucleotide in the place of the non-natural nucleotide.

Other aspects of the invention will be clear from a reading of the remainder of this document.

DEFINITIONS

As used in this specification and the appended claims, the singular forms "a," "an," and "the" include plural referents unless the context clearly dictates otherwise. Thus, for example, reference to "an oligonucleotide" includes a plurality of oligonucleotides; reference to "a probe" includes mixtures of such probes, and the like.

As used herein, a "biological sample" refers to any substance containing or presumed to contain nucleic acid (e.g., from a bacteria, virus, tissue biopsy etc.). The sample can be obtained by any means known to those of skill in the art. Such sample can be an amount of tissue or fluid, or a purified fraction thereof, isolated from an individual or individuals, including, but not limited to, for example, skin, plasma, serum, whole blood, spinal fluid, saliva, peritoneal fluid, lymphatic fluid, aqueous or vitreous humor, synovial fluid, urine, tears, blood cells, blood products, semen, seminal fluid, vaginal fluids, pulmonary effusion, serosal fluid, organs, bronchio-alveolar lavage, tumors, paraffin embedded tissues, etc. Samples also can include constituents and components of in vitro cell cultures, including, but not limited to, conditioned medium resulting from the growth of cells in the cell culture medium, recombinant cells, cell components, etc. A nucleic acid can be obtained from a biological sample by procedures well known in the art.

A "target nucleic acid sequence" refers to a polynucleotide sequence to be detected in a biological sample. The target nucleic acid can be, for example, the region (a subsequence or sequence) of a nucleic acid that is fully or partially complementary to the hybridizing region of a reporter domain of a nucleic acid probe as described herein. The "target sequence" can be of any length at least 3 nucleotides long. The target sequence can be a portion of a larger gene sequence or other sequence to be detected.

The terms "nucleic acid" and "polynucleotide" are used interchangeably, and refer to a polymer of monomers of ribose nucleic acids (RNA) or deoxyribose nucleic acids (DNA) polymer or analogs thereof. This includes polymers of nucleotides such as RNA and DNA, as well as modified forms thereof, peptide nucleic acids (PNAs), locked nucleic acids (LNA), and the like. In certain applications, the nucleic acid can be a polymer that includes multiple monomer types, e.g., both RNA and DNA subunits. A nucleic acid can be or include, e.g., a chromosome or chromosomal segment, a vector (e.g., an expression vector), an expression cassette, a naked DNA or RNA polymer, an amplicon, an oligonucleotide, a primer, a probe, etc. A nucleic acid can be e.g., single-stranded or double-stranded, or DNA:RNA hybrids, DNA and RNA chimeric structures. There is no intended distinction in length between the term "nucleic acid," "polynucleotide," and "oligonucleotide," and the terms can be used interchangeably herein unless the context clearly dictates otherwise.

A nucleic acid is typically single-stranded or double-stranded and will generally contain phosphodiester bonds, although in some cases, as outlined herein, nucleic acid analogs are included that may have alternate backbones, including, for example and without limitation, phosphoramide (Beaucage et al. (1993) *Tetrahedron* 49(10): 1925 and the references therein; Letsinger (1970) *J. Org. Chem.* 35:3800; Sprinzl et al. (1977) *Eur. J. Biochem.* 81:579; Letsinger et al. (1986) *Nucl. Acids Res.* 14: 3487; Sawai et al. (1984) *Chem. Lett.* 805; Letsinger et al. (1988) *J. Am. Chem. Soc.* 110:4470; and Pauwels et al. (1986) *Chemica Scripta* 26:1419), phosphorothioate (Mag et al. (1991) *Nucleic Acids Res.* 19:1437 and U.S. Pat. No. 5,644,048), phosphorodithioate (Briu et al. (1989) *J. Am. Chem. Soc.* 111:2321), O-methylphophoroamidite linkages (Eckstein, *Oligonucleotides and Analogues: A Practical Approach*, Oxford University Press (1992)), and peptide nucleic acid backbones and linkages (Egholm (1992) *J. Am. Chem. Soc.* 114:1895; Meier et al. (1992) *Chem. Int. Ed. Engl.* 31:1008; Nielsen (1993) *Nature* 365:566; and Carlsson et al. (1996) *Nature* 380:207), which references are each incorporated by reference. Other analog nucleic acids include those with positively charged backbones (Denpcy et al. (1995) *Proc. Natl. Acad. Sci. USA* 92:6097); non-ionic backbones (U.S. Pat. Nos. 5,386,023, 5,637,684, 5,602,240, 5,216,141 and 4,469,863; Angew (1991) *Chem. Intl. Ed. English* 30: 423; Letsinger et al. (1988) *J. Am. Chem. Soc.* 110:4470; Letsinger et al. (1994) *Nucleoside & Nucleotide* 13:1597; Chapters 2 and 3, ASC Symposium Series 580, "Carbohydrate Modifications in Antisense Research", Ed. Y. S. Sanghvi and P. Dan Cook; Mesmaeker et al. (1994) *Bioorganic & Medicinal Chem. Lett.* 4: 395; Jeffs et al. (1994) *J. Biomolecular NMR* 34:17; *Tetrahedron Lett.* 37:743 (1996)) and non-ribose backbones, including those described in U.S. Pat. Nos. 5,235,033 and 5,034,506, and Chapters 6 and 7, ASC Symposium Series 580, Carbohydrate Modifications in Antisense Research, Ed. Y. S. Sanghvi and P. Dan Cook. Nucleic acids containing one or more carbocyclic sugars are also included within the definition of nucleic acids (Jenkins et al. (1995) Chem. Soc. Rev. pp 169-176). Several nucleic acid analogs are also described in, e.g., Rawls, C & E News Jun. 2, 1997 page 35. These modifications of the ribose-phosphate backbone may be done to facilitate the addition of additional moieties such as labeling moieties, or to alter the stability and half-life of such molecules in physiological environments.

In addition to naturally occurring heterocyclic bases that are typically found in nucleic acids (e.g., adenine, guanine, thymine, cytosine, and uracil), nucleic acid analogs also include those having non-naturally occurring heterocyclic or other modified bases, many of which are described, or otherwise referred to, herein. In particular, many non-naturally occurring bases are described further in, e.g., Seela et al. (1991) *Helv. Chim. Acta* 74:1790, Grein et al. (1994) *Bioorg. Med. Chem. Lett.* 4:971-976, and Seela et al. (1999) *Helv. Chim. Acta* 82:1640. To further illustrate, certain bases used in nucleotides that act as melting temperature (Tm) modifiers are optionally included. For example, some of these include 7-deazapurines (e.g., 7-deazaguanine, 7-deazaadenine, etc.), pyrazolo[3,4-d]pyrimidines, propynyl-dN (e.g., propynyl-dU, propynyl-dC, etc.), and the like. See, e.g., U.S. Pat. No. 5,990,303, entitled "SYNTHESIS OF 7-DEAZA-2'-DEOXYGUANOSINE NUCLEOTIDES," which issued Nov. 23, 1999 to Seela. Other representative heterocyclic bases include, e.g., hypoxanthine, inosine, xanthine; 8-aza derivatives of 2-aminopurine, 2,6-diaminopurine, 2-amino-6-chloropurine, hypoxanthine, inosine and xanthine; 7-deaza-8-aza derivatives of adenine, guanine, 2-aminopurine, 2,6-diaminopurine, 2-amino-6-chloropurine, hypoxanthine, inosine and xanthine; 6-azacytosine; 5-fluorocytosine; 5-chlorocytosine; 5-iodocytosine; 5-bromocytosine; 5-methylcytosine; 5-propynylcytosine; 5-bromovinyluracil; 5-fluorouracil; 5-chlorouracil; 5-iodouracil; 5-bromouracil; 5-trifluoromethyluracil; 5-methoxymethyluracil; 5-ethynyluracil; 5-propynyluracil, 4-acetylcytosine, 5-(carboxyhydroxymethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 7-deazaadenine, 2-methyladenine, 2-methylguanine, 3-methylcytosine, 5-methylcytosine, N6-methyladenine, 7-methylguanine, 7-deazaguanine, 5-methylaminomethyluracil, 5-methoxyaminomethyl-2-thiouracil, beta-D mannosylqueosine, 5'-methoxycarboxymethyluracil, 5-methoxyuracil, 2-methylthio-N-6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acidmethylester, 3-(3-amino-3-N-2-carboxypropyl) uracil, (acp3)w, 2,6-diaminopurine, and 5-propynyl pyrimidine, and the like.

Additional examples of modified bases and nucleotides are also described in, e.g., U.S. Pat. No. 5,484,908, entitled "OLIGONUCLEOTIDES CONTAINING 5-PROPYNYL PYRIMIDINES," issued Jan. 16, 1996 to Froehler et al., U.S. Pat. No. 5,645,985, entitled "ENHANCED TRIPLE-HELIX AND DOUBLE-HELIX FORMATION WITH OLIGOMERS CONTAINING MODIFIED PYRIMIDINES," issued Jul. 8, 1997 to Froehler et al., U.S. Pat. No. 5,830,653, entitled "METHODS OF USING OLIGOMERS CONTAINING MODIFIED PYRIMIDINES," issued Nov. 3, 1998 to Froehler et al., U.S. Pat. No. 6,639,059, entitled "SYNTHESIS OF [2.2.1]BICYCLO NUCLEOSIDES," issued Oct. 28, 2003 to Kochkine et al., U.S. Pat. No. 6,303,315, entitled "ONE STEP SAMPLE PREPARATION AND DETECTION OF NUCLEIC ACIDS IN COMPLEX BIOLOGICAL SAMPLES," issued Oct. 16, 2001 to Skouv, U.S. Pat. No. 6,001,611, entitled 'MODIFIED NUCLEIC ACID AMPLIFICATION PRIMERS," issued Dec. 14, 1999 to S. Will, and U.S. Pat. Application Pub. No. 2003/0092905, entitled "SYNTHESIS OF [2.2.1]BICYCLO NUCLEOSIDES," by Kochkine et al. that published May 15, 2003.

It is not intended that the present invention be limited by the source of a nucleic acid, polynucleotide or oligonucleotide. Such nucleic acid can be from a human or non-human mammal, or any other organism (e.g., plant, amphibian, bacteria, virus, mycoplasm, etc.), tissue, or cell line, or derived from any recombinant source, synthesized in vitro or by chemical synthesis. Again, the nucleic acid can be DNA, RNA, cDNA, DNA-RNA, locked nucleic acid (LNA), peptide nucleic acid (PNA), a hybrid or any mixture of the above. The nucleic acid can exist in a double-stranded, single-stranded or partially double-stranded form. The nucleic acids of the invention include both nucleic acids and fragments thereof, in purified or unpurified forms, including genes, chromosomes, plasmids, the genomes of biological material such as microorganisms, e.g., bacteria, yeasts, viruses, viroids, molds, fungi, plants, animals, humans, mycoplasms, and the like.

"Extension of a primer" refers to the ability of a nucleotide incorporating biocatalyst, such as a polymerase, to add nucleotides to the 3' terminus of a primer in a template-specific manner. A primer is non-extendible if, for example, the 3' end of the primer is blocked.

"Polymerase chain reaction extension conditions" refer to conditions under which primers that hybridize to a template nucleic acid are extended by a polymerase during a polymerase chain reaction (PCR) annealing step. Those of skill in the art will appreciate that such conditions can vary, and are generally influenced by ionic strength and temperature. Various PCR annealing conditions are described in, e.g., *PCR Strategies* (M. A. Innis, D. H. Gelfand, and J. J. Sninsky eds., 1995, Academic Press, San Diego, Calif.) at Chapter 14; *PCR Protocols: A Guide to Methods and Applications* (M. A. Innis, D. H. Gelfand, J. J. Sninsky, and T. J. White eds., Academic Press, NY, 1990).

The term "natural nucleotide" refers to purine- and pyrimidine-type nucleotides found in cellular DNA (e.g., cytosine (C), adenine (A), guanine (G) and thymine (T)) and in cellular RNA (e.g., cytosine (C), adenine (A), guanine (G) and uracil (U)).

The phrase "non-natural nucleotide" or "modified nucleotide" refers to a unit in a nucleic acid polymer that contains a modified base, sugar or phosphate group, or that incorporates a non-natural moiety in its structure. For example, the base, sugar or phosphate of a non-natural nucleotide may be modified according to the modifications described above for nucleic acid analog. The non-natural nucleotide can be produced by a chemical modification of the nucleotide either as part of the nucleic acid polymer or prior to the incorporation of the modified nucleotide into the nucleic acid polymer. In another approach a non-natural nucleotide can be produced by incorporating a modified nucleoside triphosphate into the polymer chain during an amplification reaction. Examples of non-natural nucleotides, by way of illustration and not limitation, include dideoxynucleotides, derivatives or analogs that are biotinylated, amine modified, alkylated, fluorophor-labeled, and the like and also include phosphorothioate, phosphite, ring atom modified derivatives, and so forth.

A nucleic acid is "complementary" in relation to another nucleic acid when at least a nucleic acid segment (i.e., at least two contiguous bases) can combine in an antiparallel association or hybridize with at least a subsequence of other nucleic acid to form a duplex. The antiparallel association can be intramolecular, e.g., in the form of a hairpin loop within a nucleic acid, or intermolecular, such as when two or more single-stranded nucleic acids hybridize with one another. In the context of the present invention, for an oligonucleotide that is "fully complementary" to particular sequence, each base of the oligonucleotide is complementary to the corresponding bases in the particular sequence in an anti-parallel manner. Certain bases not commonly found in natural nucleic acids may be included in the nucleic acids of the present invention and include, for example, inosine, 7-deazaguanine and those discussed above. In some embodiments, complementarity is not perfect (i.e., nucleic acids can be "partially complementary" rather than "fully complementary"). Stable duplexes, for example, may contain mismatched base pairs or unmatched bases. "Substantially complementary" refers to a sequence that is at least 80% (e.g., at least 80, 85, 90, or 95%) complementary to a potential binding sequence. Where not indicated, the term refers to the degree of complementarity across the entire length of the potential binding sequence.

A "primer nucleic acid" or "primer" is a nucleic acid that can hybridize to a target or template nucleic acid and permit chain extension or elongation using, e.g., a nucleotide incorporating biocatalyst, such as a polymerase under appropriate reaction conditions. Such conditions typically include the presence of one or more deoxyribonucleoside triphosphates and the nucleotide incorporating biocatalyst, in a suitable buffer ("buffer" includes substituents which are cofactors, or which affect pH, ionic strength, etc.), and at a suitable temperature. A primer nucleic acid is typically a natural or synthetic oligonucleotide (e.g., a single-stranded oligodeoxyribonucleotide, etc.). Although other primer nucleic acid lengths are optionally utilized, they typically comprise hybridizing regions that range from about 6 to about 100 nucleotides in length. Short primer nucleic acids generally require lower temperatures to form sufficiently stable hybrid complexes with template nucleic acids. A primer nucleic acid that is at least partially complementary to a subsequence of a template nucleic acid is typically sufficient to hybridize with the template for extension to occur. The design of suitable primers for, e.g., the amplification of a given target sequence is well known in the art and described in the literature cited herein. A primer nucleic acid can be labeled, if desired, by incorporating a label detectable by, e.g., spectroscopic, photochemical, biochemical, immunochemical, chemical, or other techniques. To illustrate, useful labels include radioisotopes, fluorescent dyes, electron-dense reagents, enzymes (as commonly used in ELISAs), biotin, or haptens and proteins for which antisera or monoclonal antibodies are available. Many of these and other labels are described further herein and/or otherwise known in the art. One of skill in the art will recognize that, in certain embodiments, primer nucleic acids can also be used as probe nucleic acids.

As used herein, the term "probe" refers to an oligonucleotide (or other nucleic acid sequence) which can form a duplex structure with a region of a target nucleic acid (or amplicon derived from such target nucleic acid), due to partial or complete complementarity of at least one sequence in the probe with a sequence in the target nucleic acid under suitable conditions. As defined herein, the probe can further comprise non-nucleotide components, e.g. a non-nucleoside linker. As discussed herein, the probe can be labeled or unlabeled. The 3'-terminus of the probe optionally can be designed to prohibit incorporation of the probe into a primer extension product (non-extendible). This can be achieved by using non-complementary bases or by adding a chemical moiety such as biotin or a phosphate group to the 3'-hydroxyl group of the last nucleotide, which can, depending upon the selected moiety, serve a dual purpose by also acting as a label for subsequent detection or capture of the nucleic acid attached to the label. Prohibiting extension can also be achieved by removing the 3'-OH or by using a nucleotide that lacks a 3'-OH such as a dideoxynucleotide, or by adding a bulky group that blocks extension by steric hindrance. Polynucleotides can also be rendered non-extendible, for example, by modifying the 2' end of the polynucleotide, e.g., with a phosphate or other moiety, as described for example, in any of U.S. Pat. Nos. 7,947,817 and 7,745,125.

As used herein, the term "stem loop" refers to a secondary structure comprising a stem part and an unpaired loop part. In accordance with the present invention, the stem is formed by two complementary regions of a single-stranded nucleic acid. The stem portion of a stem loop can be formed from two regions of a single nucleic acid, wherein one of the 2 regions comprises at least 3 (e.g., at least 3, at least 4, at least 5, at least 6, at least 7, or more) bases 100% complementary to the other of the two regions, thereby allowing for formation of the stem duplex under appropriate conditions. The intervening bases between the two regions can form an unpaired loop, comprising, e.g., at least three, at least five, at least seven, at least ten, or at least 20 or more bases.

The term "hybridizing region" refers to that region of at least 3 contiguous nucleotides in length of a nucleic acid that is exactly or substantially complementary to, and therefore hybridizes to, a polynucleotide.

As used herein, the term "$T_m$" refers to the "melting temperature." The melting temperature is the temperature at which one half of a population of double-stranded polynucleotides or nucleobase oligomers (e.g., hybridization complexes), in homoduplexes or heteroduplexes (i.e., duplexes that are completely or partially complementary), become dissociated into single strands (under defined ionic strength, pH and nucleic acid concentration). The prediction of a $T_m$ of a duplex polynucleotide takes into account the base sequence as well as other factors including structural and sequence characteristics and nature of the oligomeric linkages. Methods for predicting and experimentally determining $T_m$ are known in the art.

For example, a $T_m$ is traditionally determined by a melting curve, wherein a duplex nucleic acid molecule is heated in a controlled temperature program, and the state of association/dissociation of the two single strands in the duplex is monitored and plotted until reaching a temperature where the two strands are completely dissociated. The $T_m$ is determined from this melting curve. Alternatively, a $T_m$ can be determined by an annealing curve, wherein a duplex nucleic acid molecule is heated to a temperature where the two strands are completely dissociated. The temperature is then lowered in a controlled temperature program, and the state of association/dissociation of the two single strands in the duplex is monitored and plotted until reaching a temperature where the two strands are completely annealed. The $T_m$ is then determined from this annealing curve.

As used herein, the term "detectably-labeled," or "detectable label" refers to a chemical species that can be detected or can lead to a detectable response. Detectable labels in accordance with the invention can be linked to probe either directly or indirectly. In some embodiments, detectable labels are members of an interactive label pair. In some other embodiments, one member of the label pair is a fluorophore, and the other member of the label pair is a quencher.

BRIEF DESCRIPTION OF THE DRAWINGS

FIG. 5: Probes used in the Examples.

DETAILED DESCRIPTION OF THE INVENTION

I. Introduction

Figure 1A:
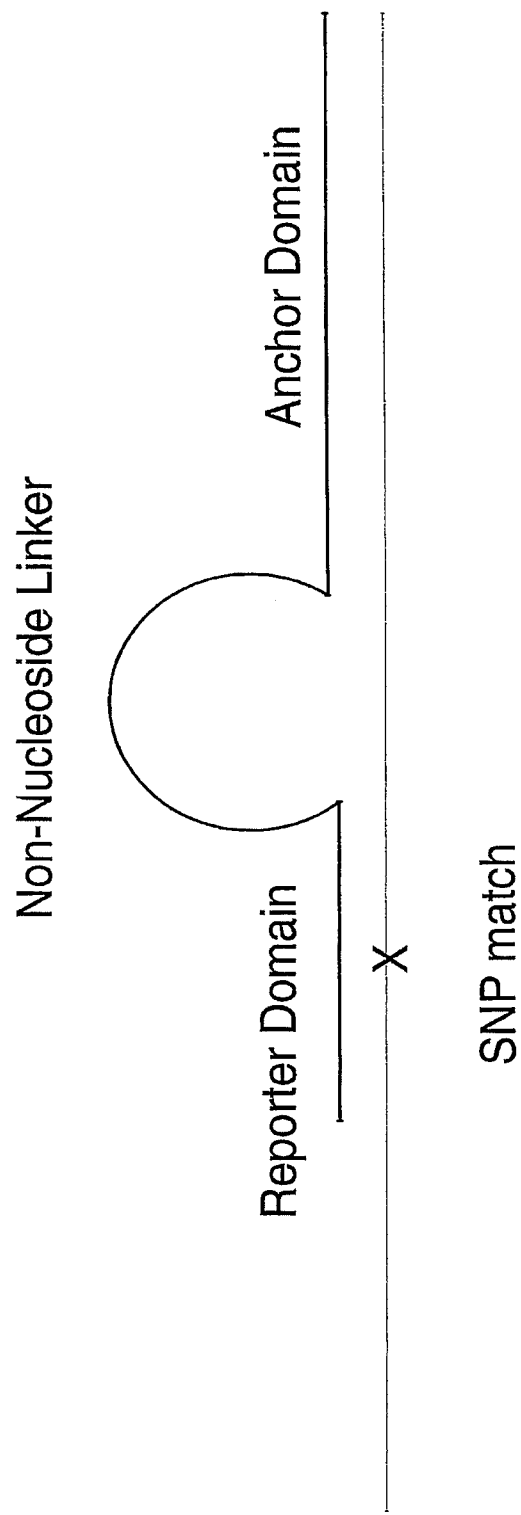
FIG. 1: (A) When the reporter domain is 100% complementary to the target nucleic acid, it hybridizes onto the target nucleic acid. As shown in the figure, the target nucleic acid sequence contains a single nucleotide polymorphism (SNP), and the reporter domain is 100% complementary to the target sequence containing the SNP. (B) When there is a SNP mismatch, e.g. the target nucleic acid sequence contains a variant or alternative alleles of the SNP, the reporter domain does not hybridize onto the target nucleic acid.
Figure 1B:
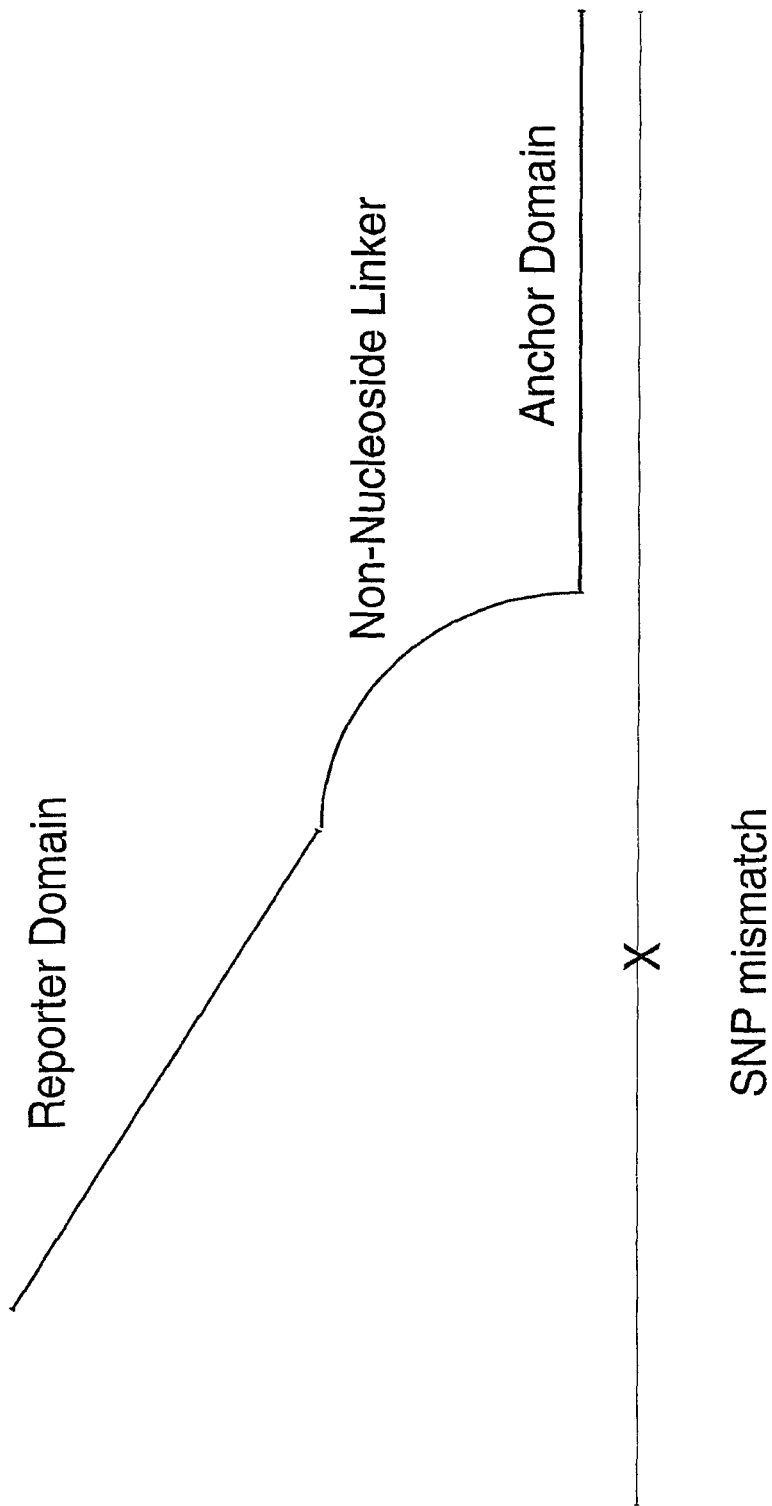

The present invention is based, in part, on the discovery that a two-domain probe having a flexible linker allows for specific detection of the presence or absence of a target nucleic acid sequence. The first domain serves as an "anchor" that drives the hybridization of the probe onto the target nucleic acid. This domain hybridizes to the target nucleic acid stably, and is tolerant of potential mismatches, or is designed to form a duplex with a region having low variability within the complementary region ("anchor-binding" region) of the target nucleic acid. The second domain serves as a "reporter" that is designed to detect the sequence of interest. The "reporter" is highly specific for the complementary region of the target nucleic acid ("reporter-binding" region), and is capable of detecting the presence or absence of the target sequence as well as differentiation of match/mismatch with the reporter binding region. The reporter domain is generally linked to a label such that one can distinguish hybridization and lack of hybridization of the reporter domain, thus detecting the presence or absence of the target sequence, or detect alterations in melting temperature, thus detecting mismatches in the probe region. The two-domain probe of this design allows for highly specific in detecting a target sequence of interest.

The present invention also provides methods for detecting a target nucleic acid with the two-domain probes. Accordingly, the methods of the present invention are useful in numerous applications including, but are not limited to, molecular diagnostics, agriculture, food testing, crop/livestock breeding, pathogen identification, drug discovery/development, and pharmacogenomics. For example, the methods of the present invention can be used in detection of particular variants of a virus or detection of a nucleic acid sequence comprising a single nucleotide polymorphism or a point mutation in various organisms.

II. Probes

The present invention relates to a probe comprising an anchor nucleic acid domain and a reporter nucleic acid domain, and further comprising a non-nucleoside linker to link the two domains. For convenience, the anchor nucleic acid domain can also be called "first domain," and the reporter nucleic acid domain can also be called "second domain" The probe of the present invention is designed to be detectably labeled to detect the presence or absence of a target nucleic acid, i.e. such that there is a change in signal from the label when the reporter domain hybridizes to the target compared to when the reporter is not hybridized to the target. By detecting and measuring the change in the detectable signal, the presence or absence of the target nucleic acid sequence can be qualitatively or quantitatively determined. By detecting alterations in melting temperature, the presence or absence of mutations or alterations of the target can be determined.

The anchor domain of the invention is designed to hybridize to an "anchor binding" sequence of the target nucleic acid under the conditions of the assay. In contrast, the reporter domain may or may not hybridize to its target "binding region" depending on whether the precise target sequence is present. The reporter domain can be designed, for example, to be complementary or at least substantially complementary to a "reporter binding" sequence of a target nucleic acid.

Depending on the reaction conditions used, one can distinguish hybridization of the reporter domain to the target versus hybridization to a target variant sequence.

The probe of the present invention can be designed to act as a primer that permits chain extension or elongation using, e.g., a nucleotide incorporating biocatalyst, such as a polymerase under appropriate reaction conditions. Alternatively, the probe can also be rendered non-extendible such that additional nucleotides cannot be added to the probe. The probe can be rendered non-extendible, for example, by modifying the 3' end of the probe such that the hydroxyl group is no longer capable of participating in elongation. The hydroxyl group of a 3' natural-occurring nucleotide simply can be modified with a variety of functional groups. For example, the 3' end of the probe can be rendered non-extendible by incorporating a nucleotide analog that lacks a 3' hydroxyl group or cannot function as a substrate of a polymerase for extension. Optionally, the probe can be rendered non-extendible by incorporating a label on its 3' end.

In some embodiments, the probe can be rendered non-extendible by incorporating a 2'-terminator nucleotide, a nucleotide analog having a blocking group at the 2'-position of the sugar moiety of the nucleotide. A "blocking group" refers to a chemical group or moiety that typically prevents the extension of a nucleic acid (i.e., a 2'-terminator nucleotide is typically non-extendible by one or more nucleotide incorporating biocatalysts). That is, once a 2'-terminator nucleotide is incorporated into a nucleic acid (e.g., at a 3'-terminus end of the nucleic acid), the blocking group prevents further extension of a nucleic acid by at least one nucleotide incorporating biocatalyst. Exemplary nucleotide incorporating biocatalysts include DNA polymerases, including but not limited to, e.g., a G46E E678G CS5 DNA polymerase, a G46E L329A E678G CS5 DNA polymerase, a G46E L329A D640G S671F CS5 DNA polymerase, a G46E L329A D640G S671F E678G CS5 DNA polymerase, a G46E E678G CS6 DNA polymerase, a ΔZO5R polymerase, a E615G Taq DNA polymerase, a Thermus flavus polymerase, a TMA-25 polymerase, a TMA-30 polymerase, a Tth DNA polymerase, a Thermus specie SPS-17 polymerase, a E615G Taq polymerase, a Thermus Z05R polymerase, a T7 DNA polymerase, a Kornberg DNA polymerase I, a Klenow DNA polymerase, a Taq DNA polymerase, a Micrococcal DNA polymerase, an alpha DNA polymerase, a reverse transcriptase, an AMV reverse transcriptase, an M-MuLV reverse transcriptase, a DNA polymerase, an RNA polymerase, a E. coli RNA polymerase, an SP6 RNA polymerase, a T3 RNA polymerase, a T4 DNA polymerase, a T7 RNA polymerase, an RNA polymerase II, a terminal transferase, a polynucleotide phosphorylase, a ribonucleotide incorporating DNA polymerase, and the like.

An exemplary blocking group is a phosphate group. Exemplary 2'-terminator nucleotides include 2'-monophosphate-3'-hydroxyl-5'-triphosphate nucleosides and 2'-monophosphate-3'-hydroxyl-5'-diphosphate nucleosides. Other 2'-terminator nucleotides are described in, e.g., U.S. Pat. Nos. 7,947,817, 7,572,581 and 7,745,125 which are incorporated by reference.

According to the present invention, the anchor nucleic acid domain and the reporter nucleic acid domain is linked by a non-nucleoside linker. Any standard technique can be used to attach the anchor nucleic acid domain or the reporter nucleic acid domain to the non-nucleoside linker. The anchor nucleic acid domain or the reporter nucleic acid domain can be linked to the non-nucleoside linker either directly or indirectly. In some embodiments, the anchor nucleic acid domain or the reporter nucleic acid domain is covalently attached to the non-nucleoside linker.

A. The Anchor Nucleic Acid Domain

The anchor nucleic acid domain of the present invention is designed to bind to a "anchor binding" sequence of a target nucleic acid in a biological sample under the conditions of the assay. Accordingly, the anchor nucleic acid domain can be designed to comprise a region that is complementary or substantially complementary to the "anchor binding" sequence of the target nucleic acid. In some embodiments of the invention, the anchor nucleic acid domain comprises, or consists of, a region that is complementary or substantially complementary to the "anchor binding" sequence within the target nucleic acid. The complementary regions can be of any length useful for the invention, including but not limited to, at least 4, 6, 8, 10, 12, 14, 16, 20 or more nucleotides, e.g., 3-50, 5-20, 5-50, or 8-25 nucleotides long.

In some embodiments of the invention, the anchor nucleic acid domain can comprise additional regions, for example, a region for attachment of detectable labels. In some embodiments, the anchor nucleic acid domain contains only one region that is complementary or substantially complementary to one "anchor binding" sequence of the target nucleic acid. In some embodiments, the anchor nucleic acid domain can contain two or more regions, each binds to a distinct "anchor binding" sequence within the target nucleic acid.

According to the present invention, the anchor nucleic acid domain (or the first domain) is designed to drive the hybridization of the probe to the target nucleic acid. In some embodiments, the composition and length of the anchor nucleic acid domain is chosen to overcome (i.e., hybridize under conditions of the method in spite of) potential mismatches between the anchor nucleic acid domain and the "anchor binding" sequence due to the infrequent polymorphisms within the "anchor binding" sequence. According to the present invention, the anchor nucleic acid domain can be of any length as long as the affinities between the anchor nucleic acid domain and the "anchor binding" sequence is sufficiently large such that they hybridize under the reaction conditions. In some embodiments, the length of the anchor nucleic acid domain is chosen so that there is sufficient specificity between the probe and the target nucleic acid such that they hybridize under the reaction conditions. In some embodiments, the hybridization between the anchor nucleic acid domain and the "anchor binding" sequence alone (i.e., whether or not the reporter domain hybridizes to the target) is sufficient to drive the hybridization of the probe onto the intended location of the target nucleic acid.

In some embodiments of the invention, the anchor nucleic acid domain is about five nucleotides to about 200 nucleotides in length. In some embodiments, the anchor nucleic acid domain is between 4 to 50 nucleotides in length. In some embodiments, the anchor nucleic acid domain is between 6 to 40 nucleotides in length. In some embodiments of the invention, the anchor nucleic acid domain is between 20 to 40 nucleotides in length. In some embodiments of the invention, the anchor nucleic acid domain is between 8 to 25 nucleotides in length. In some embodiments of the invention, the anchor nucleic acid domain is about 30 nucleotides in length. In other embodiments of the invention, the anchor nucleic acid domain is between 40 to 60 nucleotides in length. In some other embodiments of the invention, the anchor nucleic acid domain is more than 60 nucleotides in length.

The anchor nucleic acid domain can comprise natural nucleotides, non-natural nucleotides, or combinations thereof. Exemplary nucleic acids include, but are not limited to, conventional ribonucleic acid (RNA), deoxyribonucleic acid (DNA), and chemical analogs of these molecules such as a locked nucleotide analog ("LNA") and a peptide nucleic acid ("PNA"). Various nucleic acid analogs described herein can also be used for the anchor nucleic acid domain. In some embodiments of the invention, the non-natural nucleotide increases the melting temperature of the anchor domain compared to a corresponding natural nucleotide in the place of the non-natural nucleotide. Exemplary artificial bases that contribute to increased Tm are described in the art, including but not limited to, e.g., Lebedev et al., *Genetic Analysis—Biomolecular Engineering* 13:15-21 (1996); Xodo, et al., *Nucleic Acids Res.* 19:5625-5631 (1991); Froehler, et al., *Tetrahedron Lett.* 33:5307-5310 (1992); Kutyavin, et al., *Biochemistry* 35:11170-11176 (1996); Nguyen, et al., *Nucleic Acids Res.* 25:30599-65 (1997). In some embodiments of the invention, the non-natural nucleotides are propynyl-dN. In some embodiments of the invention, thymine is replaced with propynyl dU, cytosine is replaced with propynyl dC.

B. The Reporter Nucleic Acid Domain

The reporter nucleic acid domain of the present invention is designed to detect the presence or absence of a target nucleic acid sequence in a biological sample. Accordingly, the reporter nucleic acid domain can be designed to comprise a region that is complementary or substantially complementary to a "reporter binding" sequence within the target nucleic acid. As discussed herein, the anchor binding domain of the target and the reporter binding domain of the target are on the same strand of target nucleic acid. In some embodiments of the invention, the reporter nucleic acid domain comprises, or consists of, a region that is complementary or substantially complementary to a "reporter binding" sequence within the target nucleic acid. In other embodiments of the invention, the reporter nucleic acid domain comprises additional regions, for example, a region for attachment of detectable labels. In some embodiments, the reporter nucleic acid domain contains only one region that is complementary or substantially complementary to one "reporter binding" sequence of the target nucleic acid. In some embodiments, the reporter nucleic acid domain can contain two or more regions, each of which is capable of hybridizing to a distinct "reporter binding" sequence of the target nucleic acid, for example, multiple SNP regions within the target nucleic acid.

Because the reporter domain sequence is designed to be selective for a specific reporter domain-binding sequence, generally the region of the reporter domain is fully complementary to the reporter binding sequence. Alternatively, the reporter domain, in combination with the reaction conditions, can be designed so that the reporter domain hybridizes to a specific target or to the specific target and to slight (e.g., a single nucleotide) variants, but does not bind to more widely varying sequences (e.g., larger deletions or substitutions, rearrangements, more than single mismatches, etc.).

The reporter nucleic acid domain and detectable label can be designed to detect the presence or absence of any target nucleic acid of interest. The target nucleic acid can be from any source. For example, the target nucleic acid can be a viral or microbial nucleic acid. Alternatively, the target nucleic acid can also be, e.g., an animal, mammalian, human, fungal or plant nucleic acid. In some embodiments, the reporter nucleic acid domain of the present invention can be designed to detect the presence or absence of a single nucleotide polymorphism (SNP) or a mutation within the target nucleic acid. Accordingly, in some embodiments, the reporter nucleic acid domain comprises a binding region that is 100% complementary to one allele of the SNP or the mutation and the probe is used under conditions that allow for one to distinguish between binding to the one allele and other possible alleles of the SNP or the wild-type sequence.

The reporter nucleic acid domain thus can be designed to be highly specific to the "reporter binding" sequence. In some embodiments, even a single-base mismatch between the reporter nucleic acid domain and the "reporter binding" sequence can induce a signal change, either chemical or physical in nature, significant enough to facilitate the detection of the match (or the mismatch). The signal change can be a conformational change of the probe, i.e. from a random coil to a duplex formed between the reporter nucleic acid domain and the target nucleic acid. The signal change can be physically or chemically detectable. For example, the probe can be fluorescently labeled in a way that fluorescence signal can be induced or changed upon a match or mismatch. The label and the probe can be designed such that a difference in fluorescence is detected between hybridization and no hybridization between the reporter nucleic acid domain and the "reporter binding" sequence. In some embodiments, this difference does not involve a stem loop in either domain of the probe (e.g., in the absence of the target). The signal change can also be a change in the melting temperature of the hybridizing duplex formed between the reporter nucleic acid domain and the "reporter binding" sequence. $T_m$ change can be measured, for example, between a complementary duplex and a mismatched duplex formed between the reporter nucleic acid domain and the "reporter binding" sequence.

In some embodiments of the invention, the report nucleic acid domain comprises, or consists of, a region that is complementary or substantially complementary to the "reporter binding" sequence within the target nucleic acid. The complementary regions can be of any length useful for the invention, including but not limited to, at least 4, 6, 8, 10, 12, 14, 16, 20 or more nucleotides, e.g., 3-50, 5-20, 5-50, or 8-25 nucleotides long.

The reporter nucleic acid domain of the present invention can be of any suitable length. In some embodiments, to maximize the specificity for its complementary sequence, the reporter nucleic acid domain of the present invention is designed to be relatively short in length. In some embodiments, the length of the target-binding portion of the reporter nucleic acid domain is between 4 to 20 nucleotides. In some embodiments, the length of the reporter nucleic acid domain is between 6 to 12 nucleotides. In some embodiments, the length of the reporter nucleic acid domain is between 8 to 25 nucleotides. In some embodiments, the length of the reporter nucleic acid domain is between 6 to 40 nucleotides. In some embodiments of the invention, the reporter nucleic acid domain is at least 6, 7, 8, 9, 10, 11, or 12 nucleotides in length.

The present invention takes advantage of the high specificity of the reporter nucleic acid domain for the "reporter binding" sequence. Accordingly, the reporter nucleic acid domain can comprise a non-natural nucleotide to increase the binding specificity of the reporter nucleic acid domain, and therefore increase the probe differentiation between a match and a mismatch. In some embodiments of the invention, the non-natural nucleotide increases the melting temperature of the reporter domain compared to a corresponding natural nucleotide in the place of the non-natural nucleotide. In some embodiments of the invention, the non-natural nucleotide increases the difference in $T_m$ of a match and a mismatch. In some embodiments of the invention, the non-natural nucleotides are propynyl-dN. Exemplary artificial bases that contribute to increased Tm are described in the art, including but not limited to, e.g., Lebedev et al., *Genetic Analysis—Biomolecular Engineering* 13:15-21 (1996); Xodo, et al., *Nucleic Acids Res.* 19:5625-5631 (1991); Froehler, et al., *Tetrahedron*

Lett. 33:5307-5310 (1992); Kutyavin, et al., *Biochemistry* 35:11170-11176 (1996); Nguyen, et al., *Nucleic Acids Res.* 25:30599-65 (1997). For example, 2-Amino A increases Tm by about 3° C. over A, 5-Methyl-C raises the Tm about 1.3° C. over C, C-5 propynyl-C improves the Tm about 2.8° C. over C and C-5 propynyl-U increases the Tm about 1.7° C. over T. optionally, the reporter region will comprise one or more (e.g., 2, 3, 4, 5, 6, 7, 8, 9, or more) stabilizing bases, but one or no stabilizing (e.g., non-natural) bases in the portion of the reporter region to hybridize to a potentially variable sequence (e.g., a SNP or expected possible mutation).

The anchor nucleic acid domain and the reporter nucleic acid domain can adopt any conformation in the absence of a target nucleic acid. In some embodiments, neither the anchor nor the reporter domain forms a stem loop. In some embodiments of the invention, the anchor nucleic acid domain and the reporter nucleic acid domain are designed to have no particular secondary structure (e.g. a random coil). In some embodiments of the invention, some regions of these domains can hybridize to each other. For example, a region in the anchor nucleic acid domain may be complementary or partially complementary to a region in the reporter nucleic acid domain. In some embodiments of the invention, the anchor and reporter domains are less than 50% complementary. In some embodiments of the invention, the probe has a stem loop structure in the absence of a target nucleic acid, formed between complementary or partially complementary regions (e.g., regions of at least 4 contiguous nucleotides) in the anchor domain and the reporter domain. In other embodiments of the invention, the anchor domain can form a stem loop in the absence of a target nucleic acid. Alternatively, the reporter domain can form a stem loop in the absence of a target nucleic acid.

In some embodiments, neither the anchor nor the reporter domains comprise a stem loop. Thus, in some embodiments, 1. The reporter domain does not include two sequences of at least three nucleotides that are fully complementary and wherein the two sequences have at least two nucleotides intervening; and/or 2. The anchor domain does not include two sequences of at least three nucleotides that are fully complementary and wherein the two sequences have at least two nucleotides intervening.

As illustrated in the Figures, in some embodiments, the anchor is at the 3' end of the probe and the reporter is at the 5' end of the probe. While the Figures illustrate embodiments wherein the reporter is linked to the 5' end of the anchor domain, it should be appreciated that the reporter can also be designed to be linked to the 3' end of the anchor domain (making the reporter at the 3' end of the probe and the anchor at the 5' end of the probe).

C. The Non-Nucleoside Linker

A "non-nucleoside linker" separates the anchor domain and the reporter domain. A skilled artisan would recognize that any suitable non-nucleoside linker can be used. Routine experiments can be used to determine optimum characteristics for the linker. According to the present invention, the anchor domain and the reporter domain are designed to bind to regions in the target nucleic acid adjacent to each other. Therefore, in some embodiments, the anchor domain and the reporter domain can be designed to be relatively close together (e.g., no more than 1, 2, 3, 4, or 5 nucleotides intervening when the reporter and anchor domains both hybridize to the target). The linked will generally be sufficiently flexible to allow the reporter to hybridize, or not, when the anchor is hybridized to an adjacent sequence in the target. The non-nucleoside linker functions to keep the spacing between the anchor domain and the reporter domain. The spacing between the anchor domain and the reporter domain can therefore be adjusted by using a non-nucleotide linker of various lengths.

The non-nucleoside linker can be, for example, aliphatic, aromatic, aryl, cyclic, chiral, achiral, a peptide, a carbohydrate, a lipid, a fatty acid, tri-, tetra-, penta-, hexa- or poly-polyethylene glycol (HEG), or a heterocyclic moiety. Other conventional non-nucleoside linkers employ homobifunctional and heterobifunctional crosslinking reagents. Homobifunctional reagents carry two identical functional groups, whereas heterobifunctional reagents contain two dissimilar functional groups to link the biologics to the bioadhesive. A vast majority of the heterobifunctional cross-linking agents contain a primary amine-reactive group and a thiol-reactive group. Covalent crosslinking agents are selected from reagents capable of forming disulfide (S—S), glycol (—CH(OH)—CH(OH)—), azo (—N=N—), sulfone (—S(=O$_2$—), ester (—C(=O)—O—), or amide (—C(=O)—N—) bridges.

The probe of the present invention is designed to have different combinations of the anchor nucleic acid domain, the reporter nucleic acid domain and the non-nucleoside linker. In some embodiments, the linker can be attached to the terminus of the anchor nucleic acid domain or the reporter nucleic acid domain, e.g. 3' or 5' position of the anchor nucleic acid domain or the reporter nucleic acid domain. Alternatively, the linker can be attached to other, internal positions of one or both nucleic acid domains of the probe, as long as the linkage or attachment does not interfere with the functions of the probe, e.g., hybridization of the probe with the intended target nucleic acid. For example, the linker can be linked to the reporter domain within, e.g., 1, 2, 3, 4, or more nucleotides of the 3' or 5' end of the reporter domain. Similarly, the linker can be linked to the anchor domain within, e.g., 1, 2, 3, 4, or more nucleotides of the 3' or 5' end of the anchor domain. The anchor nucleic acid domain and the reporter nucleic acid domain can be attached to various positions of the non-nucleoside linker. In some embodiments, these nucleic acid domains are attached to the terminus of the linker. Optionally, they can be attached to different positions of the linker.

III. Labels

In some embodiments of the invention, the anchor domain, the reporter domain or the non-nucleotide linker is detectably labeled and thus is of further use in detecting the target sequence. As noted previously, the label is linked to the probe such that hybridization of the reporter domain (not necessarily the anchor domain) is detectable. Thus, in some embodiments, the anchor domain is not linked to a label whereas the reporter domain will generally be linked to one or more label. In some embodiments, the detectably labeled probe is used to detect and quantify the target sequence in an amplification reaction, e.g., to a real-time amplification reaction.

A wide variety of detectable labels are known. Exemplary labels include fluorescent labels (including, e.g., quenchers or absorbers), non-fluorescent labels, colorimetric labels, chemiluminescent labels, bioluminescent labels, radioactive labels, mass-modifying groups, antibodies, antigens, biotin, haptens, enzymes (including, e.g., peroxidase, phosphatase), and the like. Labels may provide signals detectable by fluorescence, radioactivity, colorimetry, gravimetry, X-ray diffraction or absorption, magnetism, enzymatic activity, and the like. Labels can be used to provide a detectable (and optionally quantifiable) signal, and which can be attached to a nucleic acid or protein.

In certain embodiments of the invention, a label is a fluorescent dye or fluorophore. Typically, a particular fluorophore can emit light of a particular wavelength following absorbance of light of shorter wavelength. The wavelength of the light emitted by a particular fluorophore is characteristic of that fluorophore. Thus, a particular fluorophore can be detected by detecting light of an appropriate wavelength following excitation of the fluorophore with light of shorter wavelength. Fluorescent labels may include dyes that are negatively charged, such as dyes of the fluorescein family, or dyes that are neutral in charge, such as dyes of the carboxyrhodamine family, or dyes that are positively charged, such as dyes of the cyanine family or the rhodamine family. Other families of dyes that can be used in the invention include, e.g., polyhalofluorescein-family dyes, hexachlorofluorescein-family dyes, coumarin-family dyes, oxazine-family dyes, thiazine-family dyes, squaraine-family dyes, chelated lanthanide-family dyes, ALEXA FLUOR® dyes, and BODIPY®-family dyes. Dyes of the fluorescein family include, e.g., FAM, HEX, TET, JOE, NAN and ZOE. Dyes of the carboxyrhodamine family include Texas Red, ROX, R110, R6G, and TAMRA. FAM, HEX, TET, JOE, NAN, ZOE, ROX, R110, R6G, and TAMRA are marketed by Perkin-Elmer (Foster City, Calif.), while Texas Red is marketed by Molecular Probes, Inc. (Eugene, Oreg.). Dyes of the cyanine family include Cy2, Cy3, Cy3.5, Cy5, Cy5.5, and Cy7 and are marketed by Amersham GE Healthcare (Piscataway, N.J.). Non-fluorescent quenchers include BlackHole Quenchers™ (BHQ), marketed by Biosearch Technologies, Inc. (Novato, Calif.), Iowa Black™, marketed by Integrated DNA Tech., Inc. (Coralville, Iowa), and BlackBerry™ Quencher 650 (BBQ-650), marketed by Berry & Assoc., (Dexter, Mich.).

Various embodiments of signaling systems using a label can be used in the present invention. A label (e.g. a fluorophore, a quencher, an intercalation dye, a fluorescein) can be attached to the anchor domain, the reporter domain, or the non-nucleoside linker. Any conformation of label(s) can be used so long as it is possible to detect a difference in signal depending on hybridization of the reporter to the reporter-binding target sequence. Examples of the signaling systems of the present invention include, but are not limited to the following embodiments.

Embodiment 1

In some embodiments, the reporter domain or the anchor domain is linked to an intercalating dye that is capable of being incorporated between the bases of a double stranded nucleic acid molecule, and which produces a signal when intercalated. Suitable fluorophores include, but are not limited to, the cyanine dyes (e.g., developed by Molecular Probes) (see, e.g., Eriksson et al, *Nucleic Acids Research* 31(21):6235-6242 (2003)), ethidium bromide, Picogreen, SYBR green, acridine and others.

When the reporter domain hybridizes to the target nucleic acid sequence (match), the reporter domain and the target sequence form a duplex and the attached dye can intercalate within the duplex, thereby generating a detectable signal. For example, when the reporter domain is 100% complementary to one allele of the SNP or a mutation in a human nucleic acid sequence, under suitable conditions, the reporter domain hybridizes with the target nucleic acid, and the intercalating dye attached to the reporter has a changed or enhanced fluorescence when it becomes intercalated. When the reporter domain is not 100% complementary to the target nucleic acid, a duplex is not formed, and the dye has a different (e.g. lower) level of fluorescence.

According to the present invention, when an intercalating dye is used, the probe is designed such that any internal folding within the probe is minimized. This is to ensure the absence of a duplex formed between the anchor domain and the reporter domain, and to help reduce any background noise.

Embodiment 2

In some embodiments, the probe is linked with a fluorescent dye and a quenching dye, wherein one dye is linked to the reporter domain and one dye is linked to the anchor domain. When the reporter domain is not hybridized to the target nucleic acid sequence (e.g. mismatch), the probe assumes a conformation such that the fluorescent dye and the quenching dye are brought in close proximity, allowing the quencher to quench signal from the fluorescent dye. When the reporter domain hybridizes to the "reporter binding" sequence (e.g. a fully complementary match between the reporter domain and the target), the fluorescent dye is separated from the quencher, allowing the probe to fluoresce. Quenching of the fluorescence can be, but need not to be, achieved by a stem loop structure formed between the anchor domain and the reporter domain. Quenching, however, can be achieved without a stem loop structure. For example, quenching can be achieved by the random coiling of the probe bringing the fluorescent dye-quenching dye pair into proximity by chance. Examples of a fluorescent dye include, but are not limited to, FAM, TAMRA, TET, ROX. Examples of a quenching dye include, but are not limited to, DABCYL. According to the present invention, the quencher can be a fluorescent quencher or a non-fluorescent quencher. Examples of a non-fluorescent quencher include, but are not limited to, BHQ, Blackberry Quencher and Iowa Black.

Figure 2:
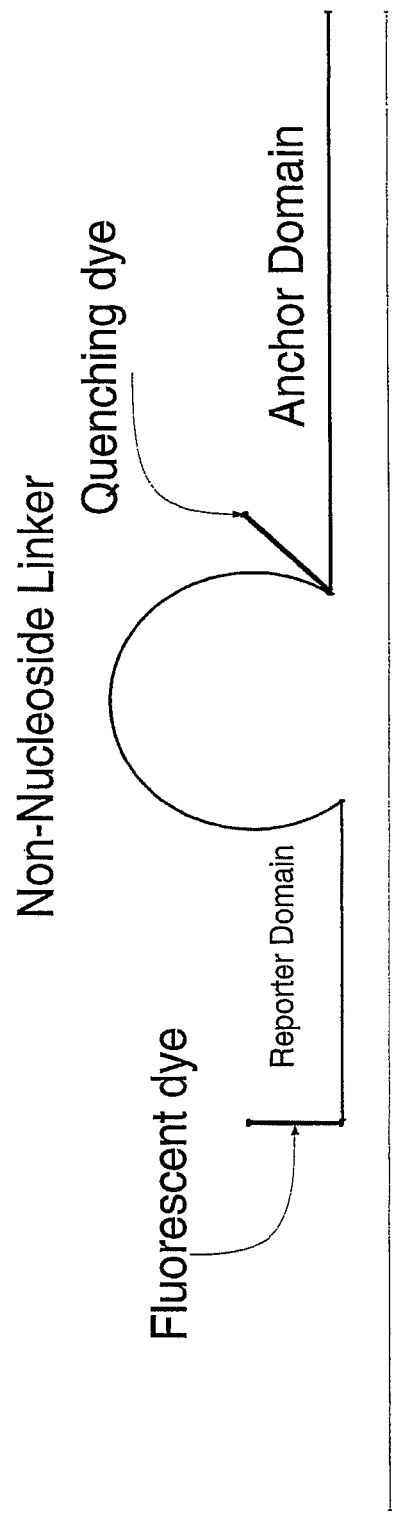
FIG. 2: Another embodiment of the labeled probe of the present invention. As shown in the figure, a fluorescent dye is attached at the 5' terminus of the reporter domain, and a quenching dye is attached at the 5' terminus of the anchor domain.

As shown in FIG. 2, in some embodiments, a fluorescent dye is linked to the 5' terminus of the reporter domain, and a quenching dye is attached on the 5' terminus of the anchor domain. In some embodiments, a fluorescent dye is linked to the 3' terminus of the reporter domain, and a quenching dye is attached on the 3' terminus of the anchor domain. In an alternative where the anchor domain is at the 5' terminus of the probe and the reporter domain is at the 3' end of the probe, the fluorescent dye is on the 3' end of the reporter domain and the quencher is at the 3' end of the anchor domain, or the fluorescent dye is on the 5' end of the reporter domain and the quencher is at the 5' end of the anchor domain. When the reporter is not hybridized to the "reporter binding" sequence, the fluorescent dye is in proximity of the quenching dye, and the fluorescence is quenched. When the reporter hybridizes to the "reporter binding" sequence, the fluorescent dye is brought away from the proximity of the quencher dye, and therefore the fluorescence is no longer quenched.

In some embodiments of the invention, the reporter domain is always labeled with a dye, either the fluorescent dye or the quenching dye. The other dye of the fluorescent-quenching pair can be attached to the anchor domain or the non-nucleoside linker.

The dyes of this embodiment can also be an energy transfer (e.g., a "FRET") pair or other pair where signal changes as a function of proximity. When an energy transfer pair of dyes is used, both dyes are fluorescent, the first a donor fluorophore and the second an acceptor fluorophore. When the donor and the acceptor are brought into close proximity, energy transfer occurs from the donor to the acceptor, which emits a signal of a different wavelength. Either the decrease in the fluorescence of the donor or the increase in fluorescence of the acceptor can be detected.

Embodiment 3

In some embodiments, the reporter domain of the probe is labeled with a fluorescent dye and a quenching dye. In some of these embodiments, the fluorescent dye and the quenching dye are designed to be in close proximity. When irradiated, the excited fluorescent dye transfers energy to the nearby quenching dye molecule rather than fluorescing. The close proximity to the fluorescent-quenching dye pair prevents emission of any fluorescence while the probe is intact.

The probe is designed to hybridize to a target nucleic acid. When the polymerase replicates a template to which the probe is bound, its 5'-3' exonuclease activity cleaves the 5' end of the probe which contains either a fluorescent dye or a quenching dye. This separates the fluorescent dye from the quenching dye, i.e. the nucleic acid fragment carrying the fluorescent dye is released into the solution and is no longer in close proximity to the quenching dye. This ends the activity of the quencher, and the fluorescent dye starts to fluoresce.

When there is a mismatch, the reporter domain of the probe does not hybridize to the "reporter binding" sequence of the target nucleic acid. In that case, the 5'-3' exonuclease activity of the polymerase does not cleave the 5' end of the probe. Consequently, the probe remains intact, the fluorescent dye remains in close proximity to the quenching dye.

Figure 3:
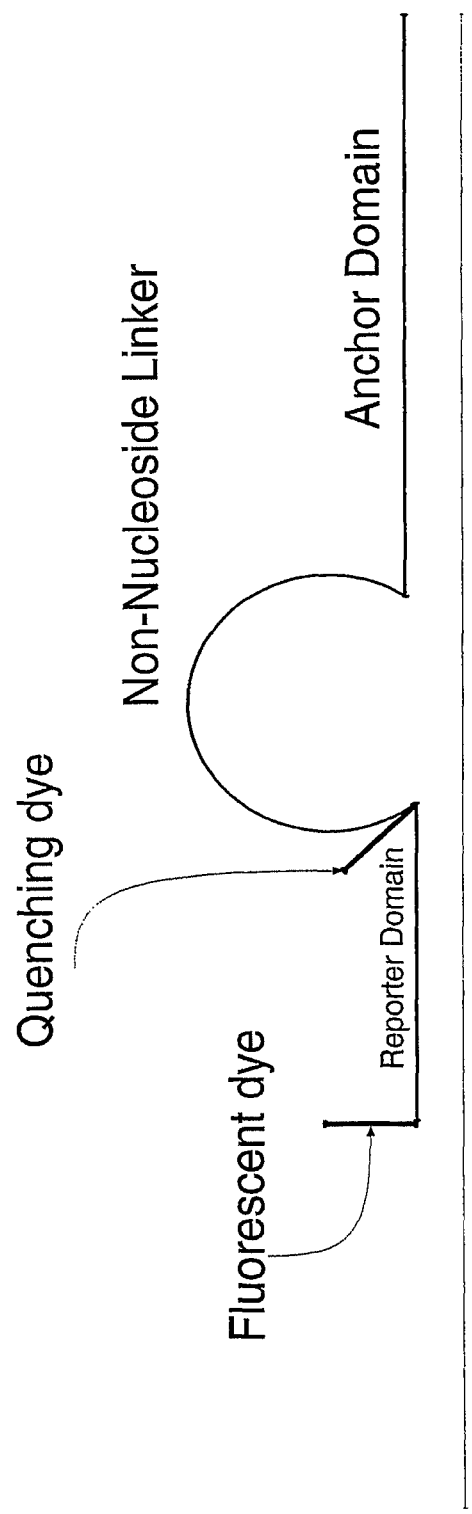
FIG. 3: Another embodiment of the labeled probe of the present invention. As shown in the figure, a fluorescent dye is attached at the 5' terminus of the reporter domain, and a quenching dye is attached at the 3' terminus of the reporter domain.

In FIG. 3, a fluorescent dye is present on the 5' terminus of the reporter domain, and a quenching dye is attached to the 3' terminus of the reporter domain. A skilled artisan would recognize that the quenching dye can be attached to any convenient location of the probe, such as on the non-nucleoside linker, or the anchor domain, as long as the quenching dye is kept in close proximity to the fluorescent dye prior to the hybridization with the target.

Figure 4:
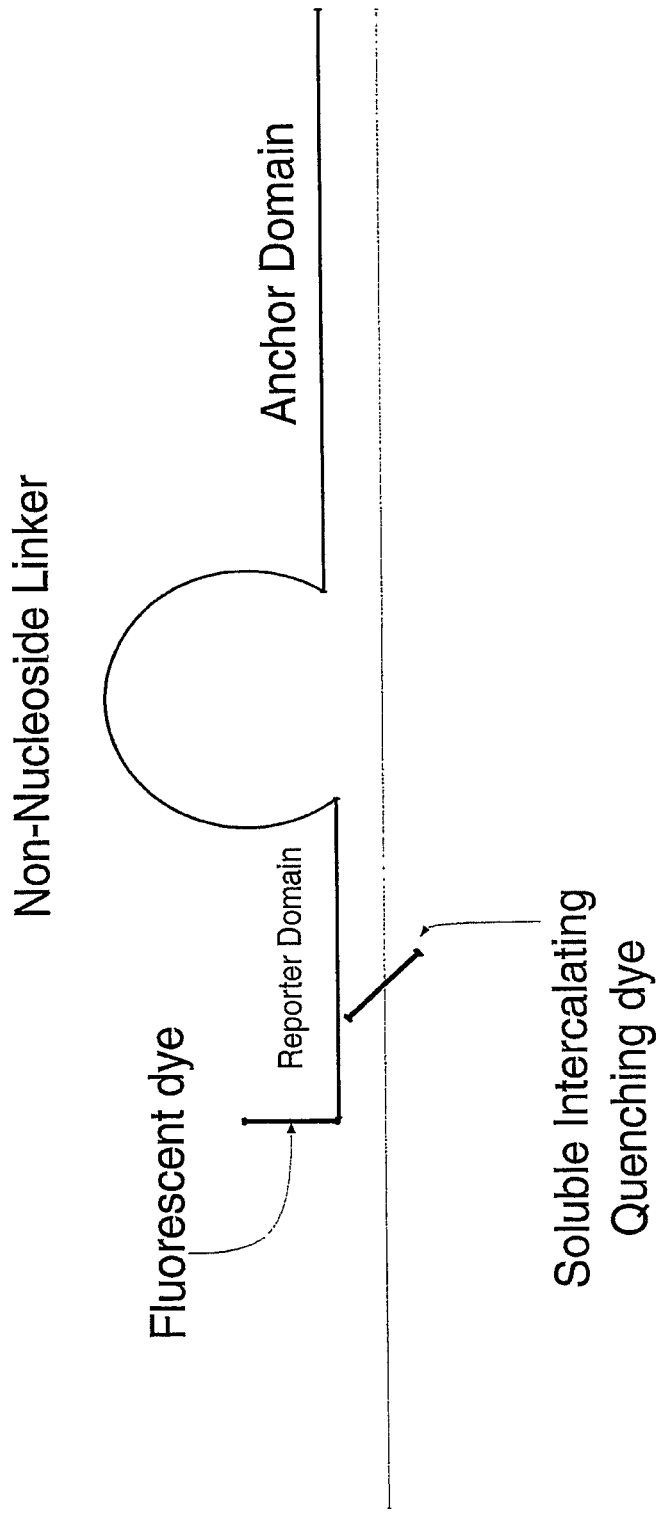
FIG. 4: Another embodiment of the labeled probe of the present invention. As shown in the figure, a fluorescent dye is attached at the 5' terminus of the reporter domain, and a soluble intercalating quenching dye is used.

In some embodiments, the quenching dye need not be covalently attached to the probe. In some cases, the reporter domain is linked to a fluorescent reporter and used in a mixture comprising a soluble (not linked to the probe) quencher. Signal is generated by the reporter when the reporter domain is not bound to the target. When the reporter binds a target, the intercalating quencher is brought in proximity to the reporter and signal is reduced. The reduction in signal is therefore an indicator of binding. This aspect is illustrated, for example, in FIG. 4. Exemplary soluble quenchers include, e.g., New Methylene Blue.

IV. Methods

The present invention relates to methods of detecting target nucleic acid sequences in a biological sample using the probes described herein. The methods of the invention can be used to detect a target nucleic acid sequence from various sources, including but are not limited to, a blood sample, a stool sample, a urine sample, a tissue sample or a biopsy. The target nucleic acids can be a human nucleic acid, a mammalian nucleic acid, a plant nucleic acid, an animal nucleic acid, a viral nucleic acid, a bacterial nucleic acid or other microbial nucleic acids.

The methods of the present invention are useful in detecting the presence or absence of an exact target nucleic acid sequence. The target nucleic acid sequence can be, for example, a site of a potential insertion, a deletion, or a nucleotide substitution. The target nucleic acid can be the results of a genome deletion, or a rare gene arrangement. Examples of a target nucleic acid sequence include, but are not limited to, a target nucleic acid sequence comprising a single nucleotide polymorphism (SNP), or a rare somatic mutation in an organism, or a ribonucleic acid sequence. In some embodiments of the invention, the methods of the invention are directed to detection of a human nucleic acid comprising a SNP or a mutation, using a probe comprising a reporter domain that is 100% complementary to one allele of the SNP or the mutation. In some other embodiments, the methods of the invention are useful for monitoring the presence or absence of particular viral or bacterial variants in an animal (including but not limited to a human) or in the environment. Examples of such infectious agents include, but are not limited to human immunodeficiency virus (HIV), Hepatitis C virus (HCV), and Human Papilloma Virus (HPV).

The methods of the invention can be used in various sequence detection techniques. For example, the methods of the invention can be used in end-point PCR product detection methods, such as genotyping. In some embodiments, the methods of the invention are used in real-time PCR techniques. In addition, the methods and probes of the invention can be used in hybridization analysis, e.g. dissociation analysis by measuring the melting or annealing curve. In some embodiments of the invention, the detection of the target nucleic acid comprises measuring the alteration of the fluorescence generated by the probes of the invention. In some embodiments, asymmetric PCR (where one primer is in excess of a second primer) is used to generate the appropriate template strand that is complementary to the probe of the invention.

In some embodiments of the invention, the detection of the target nucleic acid comprises measuring the melting temperature of a complex formed between the reporter domain and the "reporter binding" sequence. The melting temperature of the reporter domain to a target will depend on how complementary the reporter domain is for its target. If the target is fully complementary, the melting temperature will be higher than if there is one or more mismatch between the reporter and the target. In cases were the most likely target alternatives are known (for example, where two different alleles of a SNP could be present in the target), the reporter sequence can be designed to optimize the melting temperature difference between the different options. For example, the reporter domain can include one or more stabilizing bases such that the difference in the melting temperature between the reporter domain and possible (e.g., likely) target sequences are accentuated. In some examples, the difference in $T_m$ of the reporter domain can be around at least 1° C., 2° C., 3° C., 4° C., 5° C., or 8° C. In some embodiments of the invention the difference in $T_m$ of the reporter domain is around 10° C. or more.

To achieve a higher differentiation of match and mismatch, the difference in $T_m$ of the reporter domain between match and mismatch can be further increased by substituting natural, complementary nucleotides with non-natural, complementary nucleotides. In some embodiments of the invention, the numbers and types of the non-natural nucleotide substitutions are chosen to achieve, not only a higher differentiation between match and mismatch, but also a higher differentiation between different types of mismatches. For example, methods using a reporter domain comprising non-natural nucleotide can be used to differentiate between mismatches at different positions. In some embodiments of the invention, the reporter domain have 1, 2, 3, 4, 5, 6, or more non-natural, complementary nucleotides.

V. Reaction Mixtures

The present invention also provides reaction mixture involved in the methods of the invention. An exemplary reaction mixture comprises, for example, a nucleic acid from a biological sample (e.g., a target nucleic acid sequence comprising an anchor binding region and a reporter binding region) and a detectably-labeled probe as described herein comprising an anchor domain and a reporter domain. To detect the presence or absence of the target nucleic acid, particularly the presence or absence of the reporter binding region, the probe is designed such that the reporter domain comprises a sequence complementary to the reporter binding region, and the anchor domain comprises a sequence complementary to the anchor binding region. In some embodiments of the invention, neither domain of the probe forms a stem loop in the absence of a target nucleic acid and, optionally, the probe is not extendible by a DNA polymerase.

In some embodiments, the reaction mixture of the present invention can be a reaction mixture for amplification of the target nucleic acid. Accordingly, the reaction mixture comprises at least one or more of a target nucleic acid, nucleoside triphosphates (e.g., dATP, dTTP, dCTP, dGTP), a DNA polymerase and/or oligonucleotide primer.

In some embodiments of the invention, the probe of the invention is extendible, and functions as a primer.

VI. Kits

The present invention also provides kits for use in the methods of the invention. The kits of the invention can include one or more of the two-domain probes of the invention as described herein, optionally in combination (in the same or in an additional vessel) with one or more other reagents as described herein. In some embodiments, the kit is compartmentalized for ease of use and contains at least one container providing a probe of the present invention as described herein. One or more additional containers providing additional reagent(s) can also be included. Such additional containers can include any reagents or other elements recognized by the skilled artisan for use in primer extension procedures in accordance with the methods described above, including reagents for use in, e.g., nucleic acid amplification procedures (e.g., PCR, RT-PCR), DNA sequencing procedures, or DNA labeling procedures. The kit can comprise, for example, a polynucleotide comprising a target sequence. In some embodiments, the kit further includes a container providing a 5' sense primer hybridizable, under primer extension conditions, to the target sequence, and/or a primer pair comprising, e.g., a 5' sense primer and a corresponding 3' antisense primer. In some embodiments, the kit further includes a container providing a soluble intercalating quencher. In other, non-mutually exclusive variations, the kit includes one or more containers providing free nucleotides (conventional and/or unconventional). In specific embodiments, the kit includes alpha-phophorothioate dNTPs, dUTP, dITP, and/or labeled dNTPs such as, e.g., fluorescein- or cyanin-dye family dNTPs. In still other, non-mutually exclusive embodiments, the kit includes one or more containers providing a buffer suitable for a primer extension reaction.

The following examples, references, and figures are provided to aid the understanding of the present invention, the true scope of which is set forth in the appended claims. It is understood that modifications can be made in the procedures set forth without departing from the spirit of the invention.

VII. Examples

An experiment was designed to test a number of novel probe constructs, designated "Cobra" probes. The Cobra probes have a 5' (reporter) sequence and a 3' (anchor) sequence linked to each other by a hexaethylene glycol (BEG) linker. The Cobra probes were designed to hybridize to a template sequence wherein the 5' (reporter) end of the Cobra probe is substantially complementary to a target sequence in the template. The target sequence can potentially vary, depending on which template is present. The area of potential variability is referred to as the "variable region." This aspect is discussed in more detail below.

The 3' (anchor) sequence of the Cobra probe is designed to be complementary to a sequence of the template that is 5' (on the template) from the target sequence. As designed, the anchor sequence of the Cobra probe is fully complementary to any of the templates used in the experiment.

Each Cobra probe is labeled at its reporter (in this case 5') end with fluorescein. The quencher is represented by New Methylene Blue, a soluble quencher added to the reaction mixture.

Various Cobra probe versions were generated with, or without, stabilizing bases as follows:
  5NS-CBRA-USRV contained no stabilizing bases in the 9 base reporter region;
  6ST-CBRA-USRV contained 7 stabilizing bases in the 9 base reporter region
  7ST-CBRA-USRV contained 7 stabilizing bases in the 9 base reporter region, but no stabilizing bases in the center of the reporter region corresponding to the variable region in the template.
See, FIG. 5.

Asymmetric PCR was used to amplify template DNA from one of several template sources as follows:
  pK61WT—having the template to generate an amplicon shown in FIG. 5 (second line), including underlined AAC, sequence matching (complementary to) the reporter domain of the probe.
  pK61C3—having template to generate an amplicon shown in FIG. 5, but wherein the underlined bases are cAC, sequence mismatched with the reporter domain of the probe
  pK61T3—having template to generate an amplicon shown in FIG. 5, but wherein the underlined bases are tAC, sequence mismatched with the reporter domain of the probe
  pK61G2—having template to generate an amplicon shown in FIG. 5, but wherein the underlined bases are AgC, sequence mismatched with the reporter domain of the probe
  pK61T1—having template to generate an amplicon shown in FIG. 5, but wherein the underlined bases are AAt, sequence mismatched with the reporter domain of the probe
  pK61A1—having template to generate an amplicon shown in FIG. 5, but wherein the underlined bases are AAa, sequence mismatched with the reporter domain of the probe The amplification reactions were performed in the presence of 21 μM New Methylene Blue and the Cobra probes. The melting temperatures of the resulting reporter/amplicon hybrids were determined using change in fluorescence (New Methylene Blue quenches the Cobra probe fluorescein, but only when the probe portion of the Cobra probe is hybridized to the template). Results are shown in the tables below.

TABLE

Tm Data for the 3 COBRA Probes vs. WT and Mutant amplicons in Post-PCR Melt Analysis

|  | pKWT | pK61C3 | pK61T3 | pK61G2 | pK61G1 | pK61T1 | pK61A1 | Blank |
|---|---|---|---|---|---|---|---|---|
| Tm Average | | | | | | | | |
| 5NS-CBRA-USRV* | 46.7 | 47.7 | 50.7 | 49.7 | 48.7 | 49.1 | 48.5 | 48.8 |
| 5NS-CBRA-USRV§ | 61.5 | 47.7 | 50.7 | 49.7 | 48.7 | 49.1 | 48.5 | 48.8 |
| 6ST-CBRA-USRV | 69.0 | 66.1 | 66.3 | 66.7 | 66.1 | 66.3 | 66.3 | 59.7 |
| 7ST-CBRA-USRV | 68.1 | 65.9 | 65.9 | 66.3 | 60.7 | 60.8 | 60.7 | 58.0 |
| Tm St. Dev. | | | | | | | | |
| 5NS-CBRA-USRV* | 0.2 | 0.7 | 0.2 | 1.0 | 0.0 | 0.0 | 0.2 | 0.2 |
| 6ST-CBRA-USRV | 0.2 | 0.2 | 0.0 | 0.0 | 0.2 | 0.0 | 0.0 | 0.5 |
| 7ST-CBRA-USRV | 0.2 | 0.0 | 0.0 | 0.0 | 0.0 | 0.2 | 0.0 | 0.5 |
| Tm difference mutant vs WT | | | | | | | | |
| 5NS-CBRA-USRV* | — | 1.0 | 4.0 | 3.0 | 2.0 | 2.4 | 1.9 | 2.1 |
| 5NS-CBRA-USRV§ | — | −13.5 | −10.8 | −11.8 | −12.8 | −12.4 | −13.0 | −12.7 |
| 6ST-CBRA-USRV | — | −2.9 | −2.7 | −2.3 | −2.9 | −2.7 | −2.7 | −9.3 |
| 7ST-CBRA-USRV | — | −2.3 | −2.3 | −1.9 | −7.4 | −7.3 | −7.4 | −10.2 |

*5NS-CBRA-USRV has two peaks lower (1st) peak used for these calculations
§Higher second peak used for these calculations For this experiment, the best results obtained were from the Cobra probe (7ST) comprising stabilizing bases in the reporter region, but no stabilizing bases that hybridize to the potentially variable region of the target sequence. This probe allowed one to distinguish the "wildtype" from mutants and also allowed one to distinguish between the mutants.

The 6ST probe (having 7 stabilizing bases in the reporter region, including stabilizing bases in the variable region) was able to distinguish between "wildtype" and "mutant", but was not able to distinguish between mutants.

The 5NS probe (lacking stabilizing bases) was not able to distinguish between wildtype and mutant in this experiment.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A method of detecting the presence or absence of a target nucleic acid in a biological sample, the method comprising:
   a) contacting a detectably-labeled probe comprising an anchor nucleic acid domain and a reporter nucleic acid domain with the sample; and
   b) detecting the presence or absence of binding of the probe to the target nucleic acid,
      wherein the anchor and reporter domains are linked by a non-nucleoside linker, and neither the anchor nor the reporter domain forms a stem loop in the absence of the target nucleic acid; and
      wherein the probe is not extendible by a polymerase; and the linker is linked to the anchor domain within 2 nucleotides of the 5' end of the anchor domain and the linker is linked to the reporter domain within 2 nucleotides of the 3' end of the reporter domain, wherein the anchor domain is not linked to a detectable label; and
      each of the anchor domain and the reporter domain comprises a contiguous sequence of at least 6 nucleotides complementary to the same strand of the target nucleic acid.

2. The method of claim 1, wherein each of the anchor domain and the reporter domain comprises a contiguous sequence of at least 10 nucleotides complementary to the same strand of the target nucleic acid.

3. The method of claim 1 further comprising measuring the melting temperature of a complex formed by the reporter domain and the target nucleic acid when the target nucleic acid is detected in the biological sample.

4. The method of claim 1, wherein the detectably-labeled probe comprises a fluorescent label and the method further comprises contacting the probe and sample with a soluble intercalating quencher such that the quencher alters fluorescence from the label when the reporter domain forms a complex with the target nucleic acid and the target nucleic acid is in the biological sample.

5. The method of claim 1, wherein the target nucleic acid comprises a single nucleotide polymorphism (SNP) and the reporter domain is 100% complementary to the allele of the SNP.

6. The method of claim 1, wherein the reporter domain of the probe comprises at least one non-natural nucleotide and the non-natural nucleotide increases the melting temperature of the reporter domain.

7. The method of claim 1, wherein the linker is polyethylene glycol.

* * * * *

SEQUENCE LISTING

```
<160> NUMBER OF SEQ ID NOS: 2

<210> SEQ ID NO 1
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
tgtgtcgaga atatccaaga gacaggtttc t                                      31

<210> SEQ ID NO 2
<211> LENGTH: 55
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
tgatggagaa acctgtctct tggatattct cgacacagca ggtcaagagg agtac           55
```